United States Patent [19]

Hamilton et al.

[11] Patent Number: 4,568,519

[45] Date of Patent: Feb. 4, 1986

[54] APPARATUS FOR PROCESSING ANALYSIS SLIDES

[75] Inventors: George R. Hamilton; Anthony P. DiFulvio, both of Rochester, N.Y.

[73] Assignee: Eastman Kodak Company, Rochester, N.Y.

[21] Appl. No.: 509,082

[22] Filed: Jun. 29, 1983

[51] Int. Cl.[4] .......................................... G01N 35/04
[52] U.S. Cl. ...................................... 422/64; 422/63; 422/67
[58] Field of Search .................................. 422/63–67, 422/99; 353/119

[56] References Cited

U.S. PATENT DOCUMENTS

| | | | |
|---|---|---|---|
| 3,526,480 | 9/1970 | Findl et al. | 23/253 |
| 3,616,264 | 10/1971 | Ray et al. | 195/127 |
| 3,937,614 | 12/1976 | Sodickson et al. | 23/253 |
| 3,973,129 | 8/1976 | Blumberg et al. | 250/461 |
| 4,056,358 | 11/1977 | Priarone et al. | 23/253 |
| 4,067,694 | 1/1978 | Blakely et al. | 23/253 |
| 4,119,381 | 10/1978 | Muka et al. | 356/244 |
| 4,152,390 | 5/1979 | Nosco et al. | 422/63 |
| 4,219,529 | 8/1980 | Tersteeg et al. | 422/65 |
| 4,224,032 | 9/1980 | Glover et al. | 23/230 |
| 4,296,069 | 10/1981 | Smith et al. | 422/65 |
| 4,298,571 | 11/1981 | DiFulvio et al. | 422/65 |

Primary Examiner—Arnold Turk
Attorney, Agent, or Firm—Dana M. Schmidt

[57] ABSTRACT

Apparatus is disclosed for processing a generally planar analysis slide in which a shuttle is adapted to remove a slide from a distributor, deposit the slide in a preconditioner and simultaneously move a slide from the preconditioner into an incubator. A picker is adapted to remove processed slides from the incubator.

In order to ensure a constant temperature within the incubator and an effective transfer of slides into and out of the incubator within a relatively short time, the shuttle and picker are located at the same station and are operable independently of each other over a common path.

11 Claims, 8 Drawing Figures

APPARATUS FOR PROCESSING ANALYSIS SLIDES

BACKGROUND OF THE INVENTION (1) Field of the Invention

The present invention relates to apparatus for the chemical analysis of substances, and more particularly to apparatus for processing analysis slides in which the analysis slides are delivered to an incubator and removed therefrom after an incubation period.

(2) Description of the Prior Art

In performing rate analyses using generally planar analysis slides, it is known to remove a slide from an incubator, take a reading of the slide, and reinsert the slide in the incubator if subsequent readings are desired. Such a method, however, is not conducive to high throughput in an automatic analyzer, and it is difficult to maintain the slide at a constant temperature during transfer of the slide between the incubator and the read device.

U.S. Pat. No. 4,224,032, discloses an analyzer for performing rate analyses in which multiple readings are taken of a slide supported on a rotor in an incubator. Slides are delivered to a load station in the incubator, and axially-movable slide holders carried on the rotor are adapted to take the slides from the load station while the rotor is moving. After analysis, a slide is discarded by moving the slide holder over a discharge chute. Although such an arrangement functions well, the loading and unloading mechanism is very complex, and the volume of the incubator must be relatively large to accommodate the movable slide holders.

SUMMARY OF THE INVENTION

The present invention overcomes the aforementioned problems in the prior art and provides apparatus for effectively transferring slides into and out of an incubator while maintaining the slides at a constant temperature.

In accordance with the present invention, there is provided apparatus for processing a generally planar analysis slide, said apparatus comprising means for receiving a slide to be processed; an incubator having a temperature controlled chamber and a slide holder therein which is adapted to receive a slide; shuttle means for moving a slide along a path from said receiving means to said slide holder; picker means for removing a slide from said slide holder after a period of incubation, said shuttle means and said picker means being operable independently of each other and along a common portion of said path; and drive means for moving said shuttle means and said picker means in timed relation to each other.

In one embodiment of the invention, the shuttle is adapted to simultaneously move one slide from a slide distributor into a preconditioner and another slide from the preconditioner into an incubator. The picker, which is operable at the same station as the shuttle, is adapted to remove processed slides from the incubator. A drive mechanism is adapted to operate the shuttle and picker in timed relation to each other.

An advantage of the present invention is that the incubator can be made more compact and the temperature can be more precisely controlled in the incubator, since the mechanisms for loading and unloading slides are located outside the incubator. The loading and unloading mechanisms are located at the same station, and thus, only one opening into the incubator is needed. A further advantage is that a processed analysis slide can be unloaded from the incubator and a new slide loaded therein in a relatively short period of time, thereby facilitating rate analysis in which a series of readings must be taken from a particular slide in a high-throughput analyzer. The relatively fast loading and unloading can be obtained since the shuttle which loads slides is operable independently of the picker which unloads the slides; thus, the shuttle can start the loading of a slide before the picker has completed its cycle.

Other features and advantages will become apparent upon reference to the following Description of the Preferred Embodiment when read in light of the attached drawings.

DESCRIPTION OF THE PREFERRED EMBODIMENT

The present invention is useful in analyzers for processing analysis slides used to perform quantitative analyses of biological fluids. A suitable analyzer is described in commonly-owned U.S. Pat. No. 4,296,070, granted on Oct. 20, 1981, the details of which are expressly incorporated herein by reference. In the operation of such analyzer, a predetermined amount of sample fluid is deposited on an analysis slide, and the slide is delivered to an incubator. After an appropriate incubation period, a change in the slide is sensed, the amount of change being proportional to a particular analyte in the sample fluid.

The invention is particularly useful with analysis slides used to perform rate analyses in which a series of readings are taken of a particular slide to determine the rate of colorimetric change in the slide, the rate of change being proportional to a particular analyte contained in a sample fluid. An analysis slide for performing rate analyses is disclosed in U.S. Pat. No. 4,258,001 granted on Mar. 24, 1981.

Another type of analysis slide which can be used with the present invention is disclosed in U.S. Pat. No. 4,053,381, granted on Oct. 11, 1977. This patent describes an analysis slide of the type which is used to potentiometrically designate the activity of ions in a liquid.

The present invention can also be used with a test element of the type disclosed in U.S. Pat. No. 3,992,158, granted on Nov. 16, 1976. The test element disclosed in this patent is formed as a multi-layered element containing the necessary reagents for reaction with components in a biological fluid, such as blood serum, deposited thereon. Certain reactions colorimetrically produce a change in optical density in the element which is sensed by a reflectometer, the amount of light reflected from the element varying in accordance with the reaction and being indicative of the amount of the particular analyte present in the fluid.

Terms such as "up," "down," "lower," "vertical," "horizontal" and "bottom" as used herein, refer to the orientation of parts when the apparatus of the present invention is positioned in the normal position of use.

Figure 1:
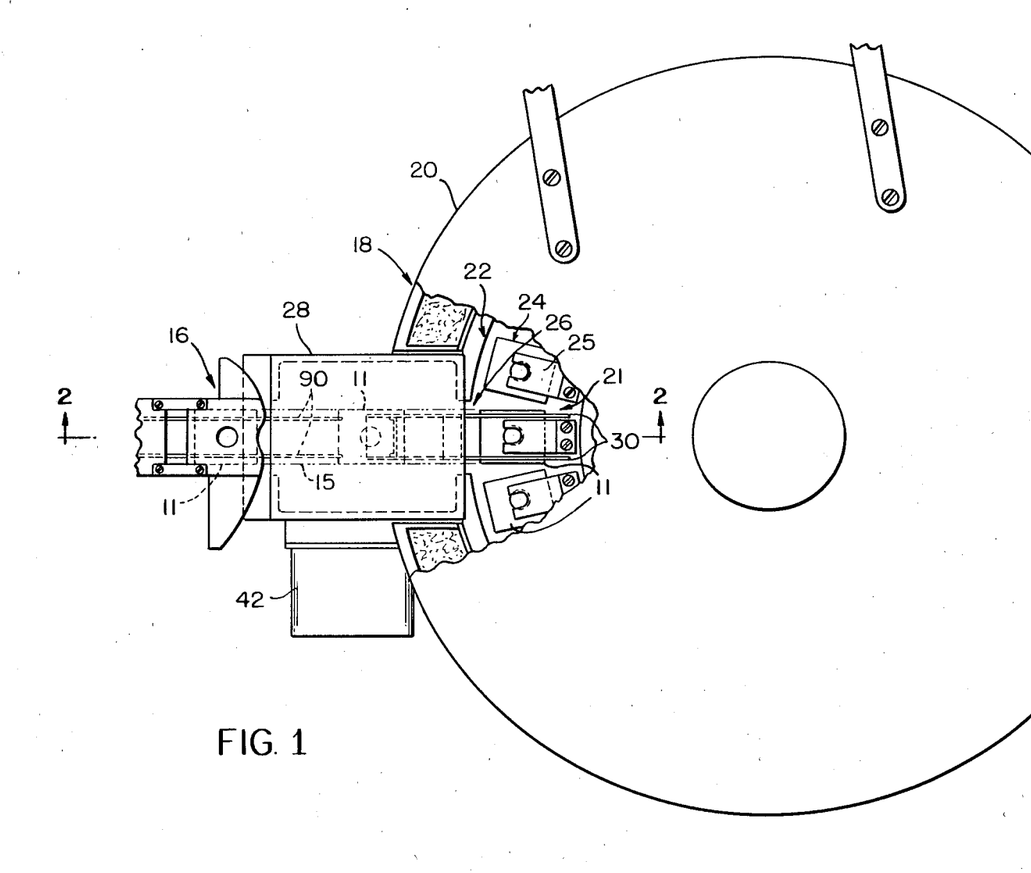
FIG. 1 is a top plan view of the apparatus of the present invention, with portions broken away to more clearly show certain elements.
Figure 2:
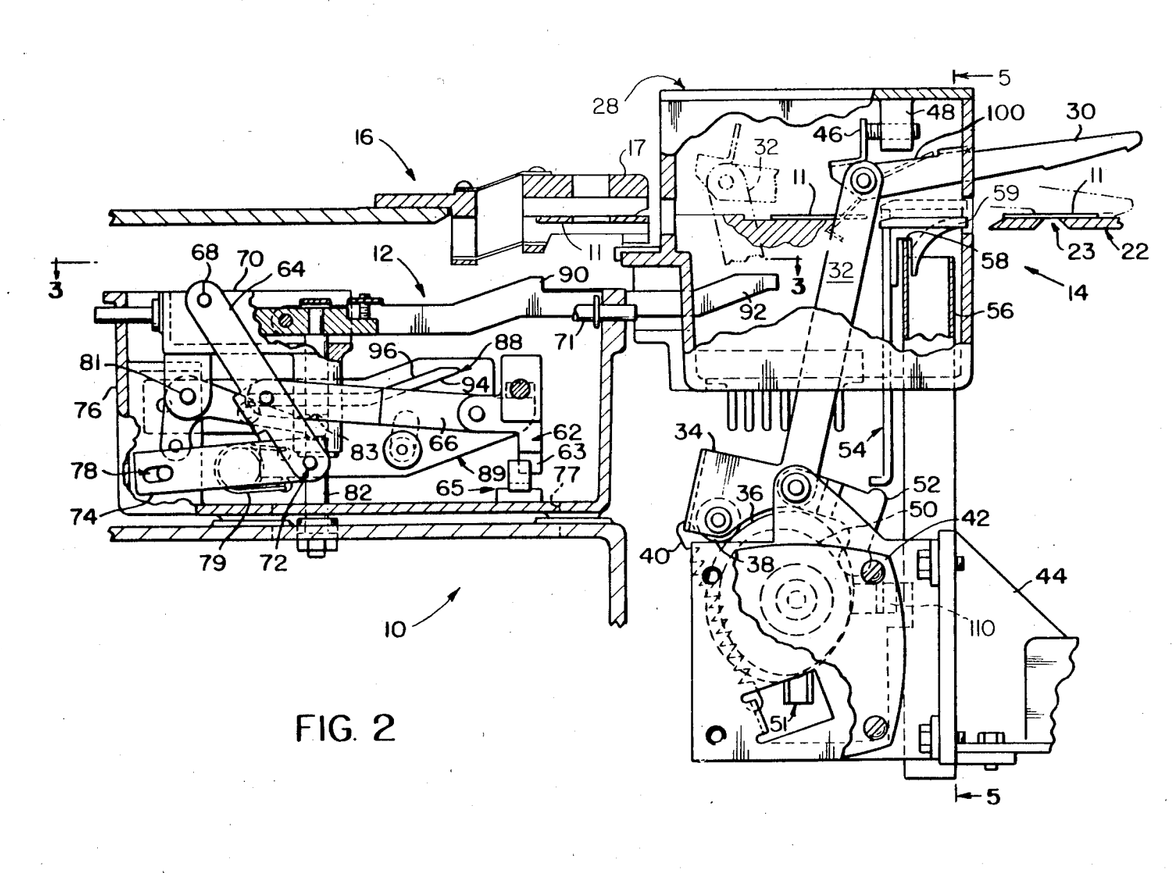
FIG. 2 is a sectional view taken along the line 2—2 in FIG. 1.

In accordance with the preferred embodiment of the present invention, there is shown in FIGS. 1 and 2 an apparatus 10 for use in processing analysis slides 11; apparatus 10 comprises a slide distributor 16 which is adapted to receive a slide 11 to be processed, and a shuttle 12 for removing a slide 11 from slide distributor 16. Slides from distributor 16 are first moved by shuttle 12 into a preconditioner 28 and then into incubator 18. Preconditioner 28 serves to bring the temperature of slides 11 to, or near to, the temperature of incubator 28. A picker 14 removes slides 11 from incubator 18 after processing.

Incubator 18 is constructed generally as disclosed in U.S. Pat. No. 4,269,069, granted on Oct. 21, 1981, the details of which are expressly incoporated herein by reference. Incubator 18 comprises a generally cylindrical housing 20 which defines a temperature-controlled chamber 21 having a disc-shaped rotor 22 mounted therein. Rotor 22 is adapted to be rotated in a horizontal plane by a drive means (not shown). Incubator 18 is adapted to maintain analysis slides 11 at a constant temperature, for example 37° C.; a blanket heater (not shown) is mounted in housing 20 to provide heat to incubator 18, and cooling is provided by thermoelectric devices (not shown) also mounted in housing 20. Housing 20 is constructed to enclose rotor 22 such that the air space in chamber 21 is at a minimum, thereby facilitating temperature control in incubator 18. Rotor 22 comprises a plurality of slide holders 24; each of the holders 24 includes a pressure pad 25 which is adapted to be biased against a slide 11 to releasably hold the slide 11 in position during the processing thereof.

Incubator 18 is particularly suitable for performing rate analyses in which a series of reflection readings are taken of a slide 11; rotor 22 comprises an opening 23 under each slide 11, and readings are taken of the slides 11 as they are rotated past a reflectometer (not shown). Incubator 18 is adapted to operate on a series of twelve-second cycles in which rotor 22 makes approximately two revolutions every ten seconds; the rotor 22 is stopped for approximately two seconds after the two revolutions for the removal and loading of slides 11. Rotor 22 is stopped with a slide holder 24 in a load station 26 where a processed slide 11, i.e. a slide on which all desired readings have been taken, is removed by picker 14; a new slide 11 is then moved from preconditioner 28 into incubator 20 by shuttle 12. Slides 11 are moved from distributor 16 to incubator 18 on a support structure 17 along a path 15 (FIG. 1 and FIG. 2).

Figure 5:
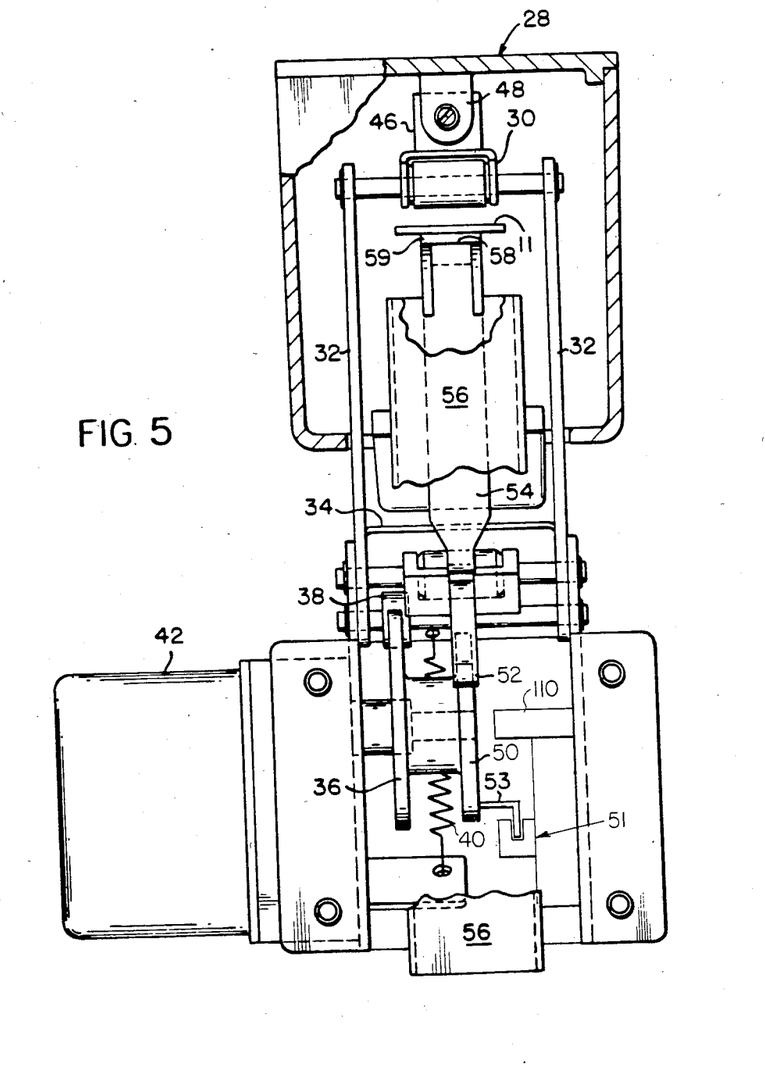
FIG. 5 is a sectional view taken along the line 5—5 in FIG. 2.

When rotor 22 is stopped with a processed slide 11 in station 26, picker 14 is actuated to remove the slide 11 from rotor 22. As shown in FIGS. 1, 2 and 5, picker 14 comprises a pair of fingers 30 which are adapted to straddle the pressure pad 25 in removing a slide 11 from incubator 20. Fingers 30 are pivotally mounted to a pair of rocker arms 32, and the fingers 30 are biased in a clockwise direction, as viewed in FIG. 2, by a spring 100. Rocker arms 32 are connected to a follower 34 which engages a cam 36 through a roller 38, and the roller 38 is biased into contact with cam 36 by a spring 40. Cam 36 is rotated by a synchronous motor 42 mounted on a frame member 44. As cam 36 is rotated, rocker arms 32 oscillate between a home position, shown in solid lines in FIG. 2, and a retracted position shown in phantom in FIG. 2. Picker 14 passes through one complete cycle as rocker arms 32 move from the home position to the retracted position and back to the home position. As rocker arms 32 approach the home position, a flange 46, connected to fingers 30, abuts against a stop 48 to move fingers 30 to an elevated position in which the fingers 30 do not interfere with the rotation of rotor 22. In the first part of the cycle of picker 14, flange 46 moves away from stop 48 and the fingers 30 drop into the position shown in dot-and-dash lines in FIG. 2.

Picker 14 is adapted to complete a cycle in 0.8 seconds or less; thus picker 14 starts from the home position, removes a slide 11 from rotor 22, and returns to the home position within 0.8 seconds. To dispose of a slide 11 removed from rotor 22, a cam 50 keyed to cam 36 drives a follower 52 which lifts a diverter 54 into the path of slide 11 at the appropriate point in the cycle of picker 14; Diverter 54 directs the slide 11 to into a discharge chute 56.

Figure 2A:
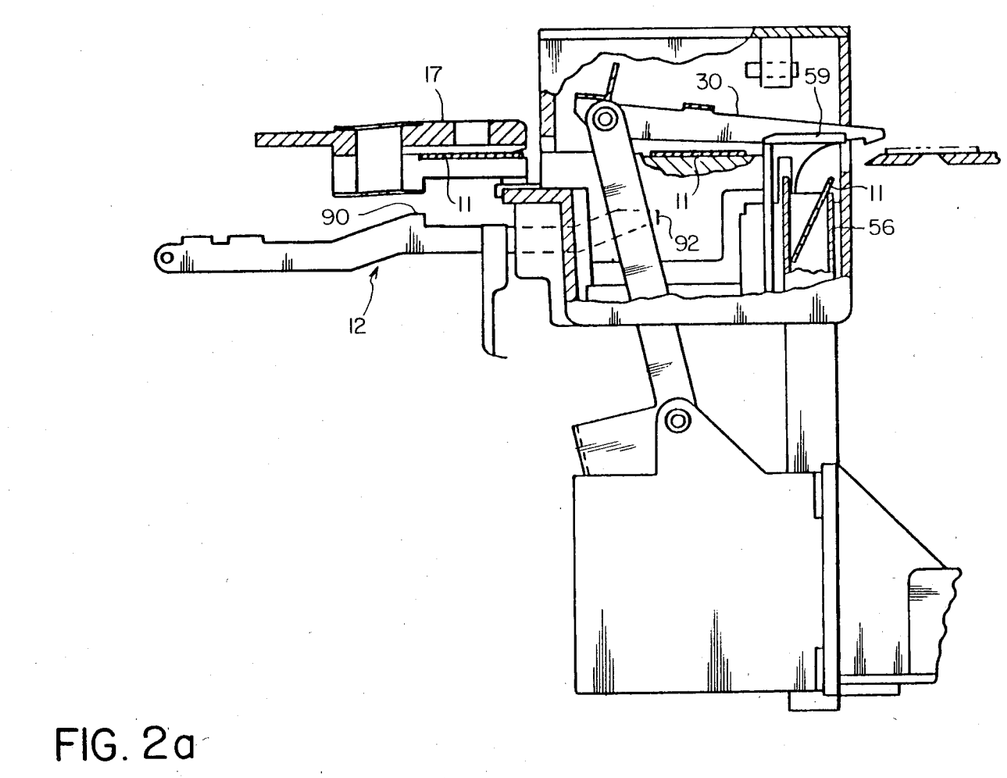
FIGS. 2A–2C are fragmentary sectional views similar to FIG. 2 but illustrating the sequential positioning of shuttle 12 and fingers 30.
Figure 2B:
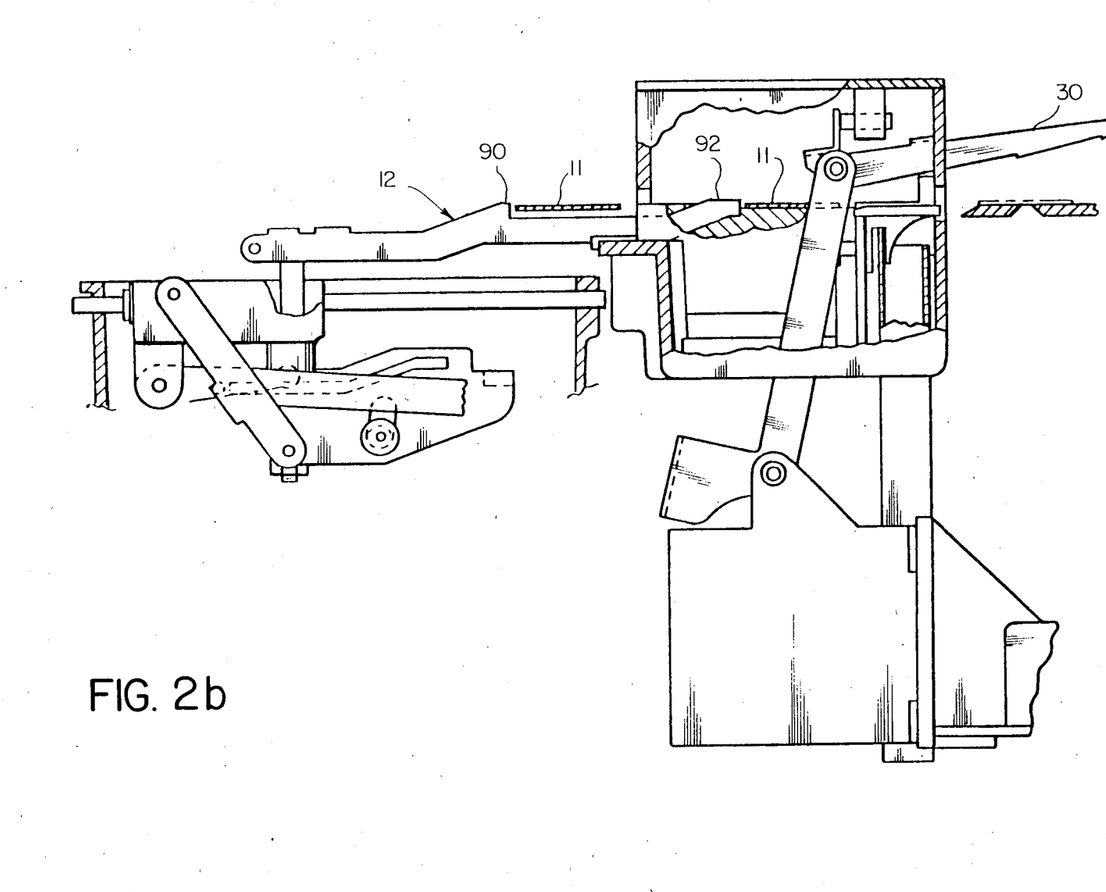

Cam 50 is designed to elevate diverter 54 into an operative position, FIG. 2A, before the picker 14 begins to move the slide 11 out of rotor 22. Diverter 54 stays in the operative position until the slide 11 is in chute 56 and then returns against a seat 58 on chute 56. A surface 59 of diverter 54, in an inoperative position (shown in FIG. 2), is in the path 15 of slide 11 as it advances from preconditioner 28 into incubator 18.

An optical sensor 51 is located to sense the position of picker 14 at a point near the end of the cycle of picker 14. When sensor 51 is actuated by a flag 53 on cam 50, a motor 60 is energized to start shuttle 12. A second sensor 110, FIG. 5, stops motor 42 when picker 14 reaches the home position.

Figure 3:
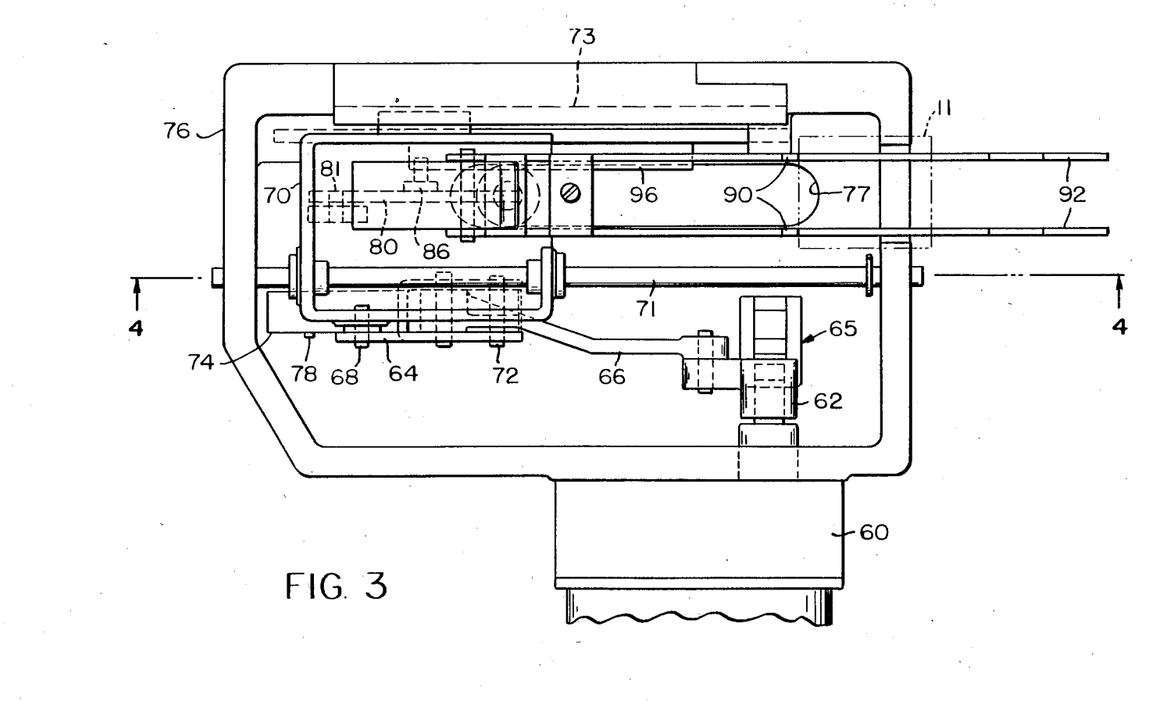
FIG. 3 is a top plan view of the shuttle.

Shuttle 12 is driven by motor 60 (FIG. 3) which drives a crank 62 connected to a shuttle lever 64 through a crank link 66. A flag 63 on crank 62 cooperates with a sensor 65 to sense the home position of shuttle 12 (shown in FIG. 2). Lever 64 is pinned at 68 to a slider 70 and at 72 to a compliance link 74 which is connected to shuttle housing 76 by means of a pin-and-slot connection 78. Slider 70 is mounted for movement on a rail 71 and a track 73 (FIG. 3). A lifter 80 is pivotally mounted at 81 on slider 70 and is connected to a retaining shaft 82 at 83. Shaft 82 extends through a groove 77 in housing 76 and is movable in a sleeve 87 on slider 70. Shaft 82 is connected to a carrier 85 having a first set of fingers 90 and a second set of fingers 92. Lifter 80 is biased in a counterclockwise direction, as viewed in FIG. 4, by a spring 84; spring 84, acting through lifter 80, biases shaft 82 and carrier 85 upwardly. A stud 86 on lifter 80 rides on a ramp 88 of an element 89 to control the raising and lowering of carrier 85 and fingers 90 and 92 thereon in a manner which will be apparent from the description which follows. Element 89 is pivotally mounted at 91 and comprises a slot 95 which receives a fixed pin 95 therein to limit pivotal movement of element 89; element 89 is biased into an "up" position by a spring 79 (FIG. 2).

Figure 2C:
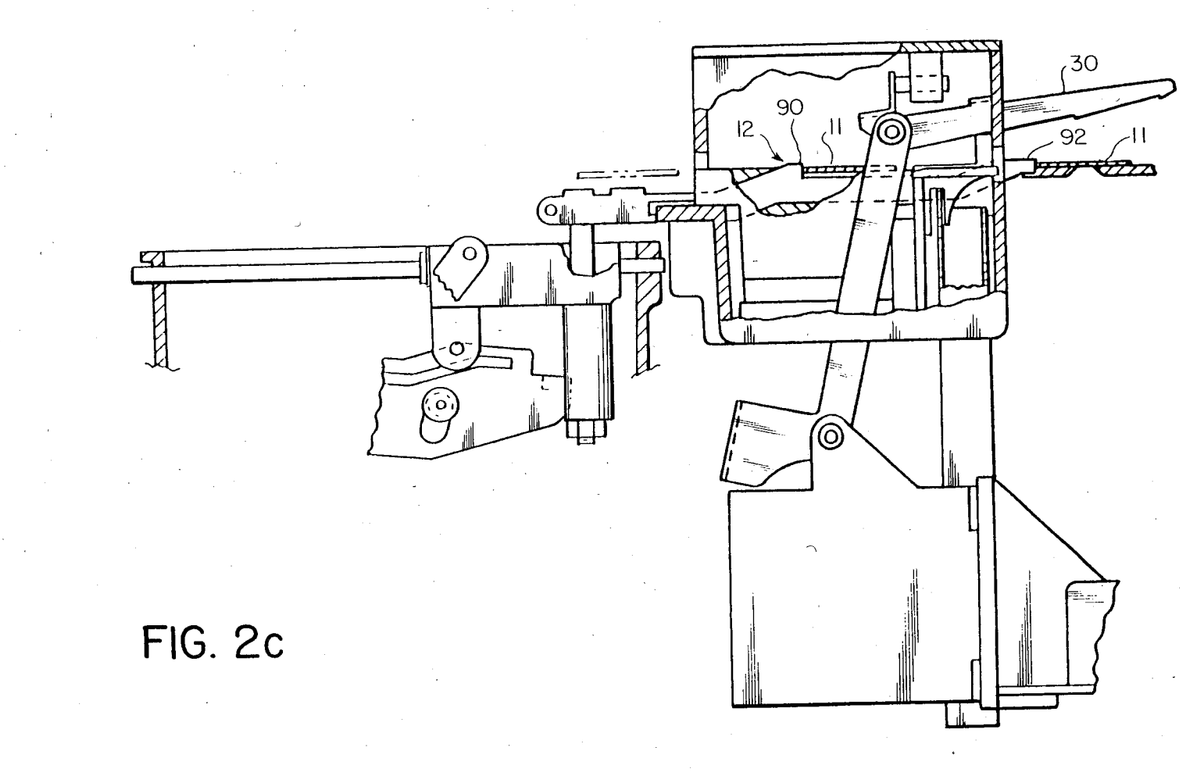
Figure 4:
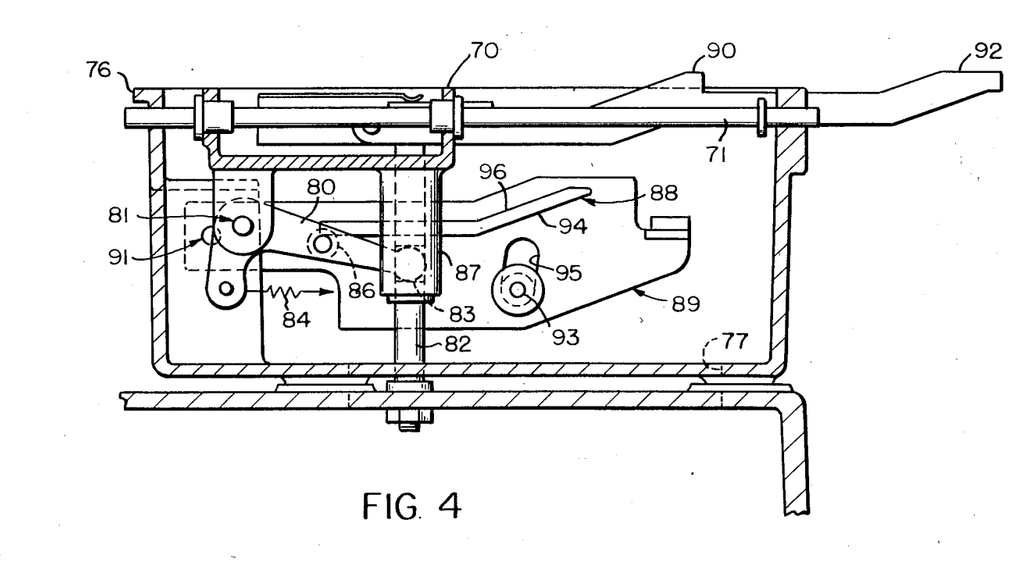
FIG. 4 is a sectional view taken along the line 4—4 in FIG. 3.

Crank 62 is rotated in a clockwise direction, as viewed in FIGS. 2 and 4, the crank 62 makes one revolution as shuttle 12 goes through one complete cycle in which slides 11 are moved from distributor 16 to preconditioner 28 and from preconditioner 28 to incubator 18. As crank 62 is rotated through one revolution, it drives fingers 90 and 92 through a generally rectangular path. At the start of the cycle of shuttle 12, the fingers 90 and 92 move rearward as crank 62 moves toward a position in line with line 66; as this is occuring, the stud 86 is sliding on an underside 94 of ramp 88. When crank 62 moves into line with link 66, stud 86 moves out of contact with ramp 88 which causes the fingers 90 and 92 to snap upward, as a result of the action of spring 84, into a forward stroke position, FIG. 2C. As crank 62 continues to rotate, fingers 90 and 92 are driven forward, fingers 90 removing a slide 11 from the slide distributor 16 and depositing the slide 11 in the preconditioner 28; simultaneously fingers 92 move a slide 11 from the preconditioner 28 to the incubator 18. Compliance link 74 reduces the impact loading of the fingers 92 on the slide 11, as the slide 11 registers in the slide holder 24.

During the forward stroke of the fingers 90 and 92 in which fingers 90 and 92, are moving toward incubator 18, the stud 86 on lifter 80 engages a top side 96 of ramp 88 which forces element 89 to pivot in a clockwise direction. As crank 62 approaches a position where it is again in line with link 66, stud 86 moves out of contact with the ramp 88, and element 89 returns to its "up" position, shown in FIGS. 2 and 4. With element 89 in its "up" position, stud 86 will engage underside 94 of ramp 88 during the return stroke of fingers 90 and 92 in which fingers 90 and 92 move to the position shown in FIG. 2. Engagement of the underside of ramp 94 will cause fingers 90 and 92 to move downward, as viewed in FIGS. 2 and 4, against the force of spring 84.

Sensors 51 and 65 monitor respectively the positions of the shuttle 12 and the picker 14, and a control means (not shown) is provided for driving the shuttle 12 and picker 14 in timed relation to each other. Such a control means is conventional in the art and could include a microcomputer (not shown) for receiving inputs from the sensors 51 and 65 and for actuating motors 42 and 60 in the proper sequence.

It is believed that the operation of apparatus 10 will be apparent from the foregoing description. Slides 11 are delivered to apparatus 10 by distributor 16 after having received a predetermined quantity of sample liquid. Shuttle 12 removes the slide 11 from distributor 16 and delivers the slide 11 to preconditioner 28. After a fixed period in preconditioner 28, the slide 11 is moved into incubator 18. In the normal operation of apparatus 10, slides are, of course, moved simultaneously from distributor 16 to preconditioner 28 and from preconditioner 28 to incubator 18. If a rate analysis is being performed, a series of readings are taken of the slide 11 in incubator 28, and the slide is then removed by picker 14 in preparation for new slide 11.

The invention has been defined in detail with reference to certain preferred embodiments thereof, but it will be understood that variations and modifications can be affected within the spirit and scope of the invention.

What is claimed is:

1. Apparatus for processing a generally planar analysis slide, said apparatus comprising:
   means for receiving a slide to be processed;
   an incubator having a temperature controlled chamber and a slide holder therein which is adapted to receive a slide;
   shuttle means for moving a slide along a path from said receiving means to said slide holder;
   picker means for removing a slide from said slide holder after a period of incubation, said slide holder after a period of incubation, said shuttle means and said picker means being operable independently of each other and along a common portion of said path;
   said picker means comprising picker fingers movable over a slide in said slide holder and down into contact with a slide in said holder to remove it therefrom, said picker fingers being adapted to return to a position over said slide holder after removal of such slide from the slide holder, said shuttle means being constructed to move under said picker fingers in moving a slide to said slide holder, and
   drive means for moving said shuttle means and said picker means in timed relation to each other.

2. Apparatus, as defined in claim 1, wherein a diverter is located in said path, and said diverter is actuatable in timed relation to said picker means to divert a slide removed from a slide holder into a disposal chute.

3. Apparatus, as defined in claim 1, wherein said picker means comprises a rocker arm which supports said picker fingers, a rotatably-driven cam, and means operatively connecting said rocker arm to said cam.

4. Apparatus, as defined in claim 1, wherein said incubator comprises a rotor having a plurality of slide holders, and said shuttle means is adapted to move a slide into a selected one of said slide holders.

5. Apparatus as defined in claim 1, wherein said shuttle means and said picker means are positioned adjacent one another at an essentially common point along the periphery of the incubator.

6. Apparatus, as defined in claim 1, wherein said drive means comprises motor means for driving said shuttle means and said picker means, control means for actuating said motor means, and said control means having sensor means for detecting the relative positions of said shuttle means and picker means.

7. Apparatus, as defined in claim 6, wherein said sensor means comprises means for sensing a predetermined position of said picker means, and said control means is adapted to effect movement of said shuttle means upon detection of said predetermined position.

8. Apparatus, as defined in claim 1, wherein a slide preconditioner is located adjacent said incubator, and said path passes through said preconditioner.

9. Apparatus, as defined in claim 8, wherein said shuttle means comprises means for simultaneously moving one slide from said receiving means to said slide preconditioner and another slide from said preconditioner to said slide holder.

10. Apparatus, as defined in claim 1, wherein said shuttle means comprises fingers adapted to engage a slide, said fingers are carried on a slider which is mounted for reciprocative movement by said drive means, and said fingers are movable relative to said slider in a direction generally perpendicular to said slider.

11. Apparatus, as defined in claim 10, wherein said shuttle means comprises a ramp, said fingers are operatively connectable to said ramp, and said ramp is adapted to effect movement of the fingers relative to said slider as said slider is moved by said drive means.

* * * * *